US009889215B2

(12) United States Patent
De Stoutz

(10) Patent No.: US 9,889,215 B2
(45) Date of Patent: Feb. 13, 2018

(54) THERMAL-TREATMENT VESSEL FOR A LIQUID CONTAMINATED BY PATHOGENIC AGENTS, DECONTAMINATION FACILITY COMPRISING SUCH A VESSEL AND ASSOCIATED DECONTAMINATION METHOD

(71) Applicant: ACTINI, Maxilly sur Leman (FR)

(72) Inventor: Frederic Laurent De Stoutz, Larringes (FR)

(73) Assignee: ACTINI, Maxilly sur Leman (FR)

( * ) Notice: Subject to any disclaimer, the term of this patent is extended or adjusted under 35 U.S.C. 154(b) by 0 days.

(21) Appl. No.: 15/106,716

(22) PCT Filed: Dec. 16, 2014

(86) PCT No.: PCT/EP2014/078067
§ 371 (c)(1),
(2) Date: Jun. 20, 2016

(87) PCT Pub. No.: WO2015/091553
PCT Pub. Date: Jun. 25, 2015

(65) Prior Publication Data
US 2016/0346414 A1    Dec. 1, 2016

(30) Foreign Application Priority Data

Dec. 20, 2013 (FR) ...................... 13 63330

(51) Int. Cl.
*A61L 2/08*    (2006.01)
*A61L 2/07*    (2006.01)
*A23L 3/16*    (2006.01)

(52) U.S. Cl.
CPC .. *A61L 2/07* (2013.01); *A23L 3/16* (2013.01)

(58) Field of Classification Search
CPC ...................................................... A61L 2/07
See application file for complete search history.

(56) References Cited

U.S. PATENT DOCUMENTS

| 2,909,985 | A | 10/1959 | Abrams |
| 3,139,812 | A | 7/1964 | Smith et al. |

(Continued)

FOREIGN PATENT DOCUMENTS

| WO | 2006/032701 A1 | 3/2006 |
| WO | 2013/133736 A1 | 9/2013 |

OTHER PUBLICATIONS

International Search Report dated Mar. 25, 2015 in PCT/EP2014/078067 Filed Dec. 16, 2014.

*Primary Examiner* — Kevin Joyner
(74) *Attorney, Agent, or Firm* — Oblon, McClelland, Maier & Neustadt, L.L.P.

(57) ABSTRACT

The invention relates to a thermal-treatment vessel (17) for pathogenic liquids intended for being filled to a predetermined level leaving a compression dome, characterised by comprising at least one pressurised-steam injector (31) positioned such as to be submerged in the liquid contaminated by pathogenic agents when the thermal-treatment vessel (17) is filled to the predetermined level with the liquid contaminated with pathogenic agents and directed toward the inside of the thermal-treatment vessel (17) with at least one tangential component so as to create a cyclonic movement of the liquid contaminated with pathogenic agents to be decontaminated.

13 Claims, 3 Drawing Sheets

(56) References Cited

U.S. PATENT DOCUMENTS

| | | | | |
|---|---|---|---|---|
| 4,830,865 A | * | 5/1989 | McFarlane | A23B 7/0053 165/87 |
| 6,332,396 B1 | * | 12/2001 | Palm | A23C 3/0375 422/26 |
| 2008/0213866 A1 | | 9/2008 | Holman et al. | |

* cited by examiner

THERMAL-TREATMENT VESSEL FOR A LIQUID CONTAMINATED BY PATHOGENIC AGENTS, DECONTAMINATION FACILITY COMPRISING SUCH A VESSEL AND ASSOCIATED DECONTAMINATION METHOD

BACKGROUND OF THE INVENTION

Field of the Invention

The present invention relates to a vessel for the heat treatment of a liquid contaminated by pathogenic agents, a decontamination facility comprising such a vessel, and an associated decontamination method.

The invention applies in particular within the context of units for treating pathogenic liquids or effluents contaminated by infectious germs or agents such as viruses, bacteria, parasites (protozoa, helminths) or even prion-type proteins, or else genetically modified organisms.

Description of the Related Art

In laboratories, the manufacture, for example of vaccines generates pathogenic effluents that must be decontaminated in a guaranteed manner before any release, for example into the wastewater network, that is to say it is necessary to be certain that after treatment the infectious germs or agents have been rendered inoffensive.

This may be carried out for example by heating the effluents in a hermetic vessel at a temperature of 135° C. and by maintaining this temperature for several minutes.

However, one of the problems of these vessels that is known consists in obtaining a homogeneous temperature in the vessel and avoiding cooler zones that may present the risk that the germs or agents will not be completely neutralized and rendered inoffensive.

Another problem of these vessels is, on the one hand, the heating time, which limits the amount of effluent that can be treated in one day and, on the other hand, the energy necessary for the heating and its associated cost.

Document U.S. Pat. No. 3,139,812 describes a method and an apparatus for continuously cooking and sterilizing liquids and suspensions. In this document, the liquid is injected into a vessel in the form of a spray into a steam mist. A liquid residual portion at the bottom is not subjected to any heating.

It should be noted that this process and this apparatus are in no way suitable for the decontamination of pathogenic liquids or effluents contaminated by infectious germs or agents such as viruses, bacteria, parasites (protozoa, helminths) or even prion-type proteins, or else genetically modified organisms. Indeed, neither the exposure time of the spray to the steam nor the heating time at a high temperature are controlled.

Furthermore, in one embodiment, the bottom of the vessel is equipped with vertical plates to avoid any swirling movement of the residual liquid in order to facilitate the discharging of the liquid through a central pipe positioned in the bottom of the vessel.

SUMMARY OF THE INVENTION

In order to at least partially overcome the failings mentioned above, one subject of the invention is an improved heat treatment vessel.

For this purpose, one subject of the invention is a vessel for the heat treatment of pathogenic liquids that is intended to be filled to a predetermined level while leaving a compression dome, wherein it comprises at least one pressurized steam injector positioned so as to immerse in the liquid contaminated by pathogenic agents when the heat treatment vessel is filled to the predetermined level with the liquid contaminated by pathogenic agents and pointed toward the inside of the heat treatment vessel with at least one tangential component so as to create a cyclonic movement of the liquid contaminated by pathogenic agents to be decontaminated.

Thus, by injecting pressurized steam, the liquid contaminated by pathogenic agents is heated, and a cyclonic effect is created during the injection of the steam.

This has the effect of homogenizing the temperature distribution inside the treatment vessel and of reducing the heating time. Furthermore, no movable mechanical element is necessary for moving the liquid, which reduces the production costs of such a heat treatment vessel and its maintenance costs.

The heat treatment vessel according to the invention may also have one or more of the following features, taken alone or in combination:

Said at least one injector is pointed perpendicular to a radial direction with respect to the axis of revolution of the heat treatment vessel.

Said at least one injector is pointed toward the inside of the heat treatment vessel with at least one component parallel to the axis of revolution of the vessel.

The injector is pointed upward, including in particular an angle of between 60° and 80°, in particular of 70° with the axis of revolution of the vessel.

The vessel comprises a support tube passing through the cylindrical wall of the heat treatment vessel and bearing said at least one injector.

The vessel comprises a vibration damper positioned between the cylindrical wall of the heat treatment vessel and the tube.

The vessel comprises filling level sensors positioned on the cylindrical wall of the heat treatment vessel.

The invention also relates to a decontamination facility comprising:

a vessel for storing the liquid contaminated by pathogenic agents, a heat treatment vessel as described above, the inlet of which is fluidically coupled to the outlet of the storage vessel, and a heat exchanger, the inlet of which is fluidically coupled to the outlet of the heat treatment vessel.

The decontamination facility may also have one or more of the following features, taken alone or in combination:

The storage vessel is positioned higher up relative to the heat treatment vessel, and the heat treatment vessel is positioned higher up relative to the heat exchanger so that the circulation of the pathogenic liquids in the facility is achieved by gravity.

The decontamination facility comprises a relief line with a safety valve, the inlet of which is coupled level with the dome of the heat treatment vessel, and the outlet of which is coupled to the storage vessel.

The outlet of the relief line is located in the lower half of the storage vessel.

The invention also relates to a process for decontaminating pathogenic liquids in a heat treatment vessel as described above:

the heat treatment vessel is filled with a liquid contaminated by pathogenic agents while leaving a gaseous expansion volume inside the treatment vessel, the liquid contaminated by pathogenic agents is heated at a temperature between 130° C. and 140° C., preferably at 135° C. for a duration of between 4 min and 6 min, preferably for 5 min, by injecting pressurized steam, the liquid thus decontaminated is discharged.

BRIEF DESCRIPTION OF THE DRAWINGS

Other features and advantages will become apparent on reading the following description of the figures, among which.

DETAILED DESCRIPTION OF THE INVENTION

On all the figures, the same elements bear the same reference numbers.

One embodiment of the present invention will now be described below with reference to the various figures.

Figure 1:
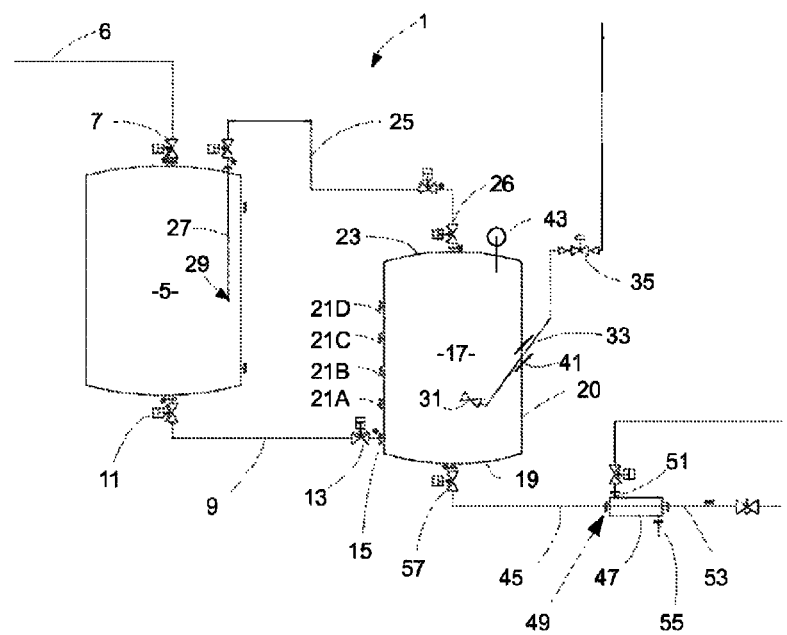
FIG. 1 is a schematic diagram of the decontamination facility according to one embodiment.

FIG. 1 shows a simplified schematic diagram of a decontamination facility 1, according to one embodiment.

Thus, the decontamination facility 1 comprises a vessel 5 for storing a liquid contaminated by pathogenic agents. This vessel 5, for example made of 316 L stainless steel, is coupled to an inlet line 6 and is used to collect the pathogenic liquids resulting for example from a production line such as a vaccine production line. A control valve 7 is positioned at the inlet of the storage vessel 5.

This storage vessel 5 is used in a way as a buffer before the treatment of the pathogenic liquids in batches.

The outlet of the storage vessel 5 is coupled via a line 9 to an inlet 15 of a heat treatment vessel 17, for example having a volume of 300 l and made of 316 L stainless steel. Two valves 11 and 13 are positioned in the line 9.

This inlet 15 is positioned in the lower portion of the heat treatment vessel 17 close to the bottom 19, so that the vessel 17 is filled via the bottom.

As is represented in FIG. 1, the storage vessel 5 is positioned higher up relative to the heat treatment vessel 17 so that the filling of the treatment vessel 17 from the storage vessel 5 may take place by gravity, according to the principle of communicating vessels. There is therefore no need for another mechanical means such as a pump to carry out the transfer of liquid between the two vessels 5 and 17.

Preferably, the volume of the vessel 5 and its height relative to the vessel 17 are selected so that when the storage vessel 5 empties into the heat treatment vessel 17, according to the principle of communicating vessels, a depth of contaminated liquid remains in the storage vessel and that the heat treatment vessel 17 is filled to a height that leaves a gaseous compression dome.

Figure 2:
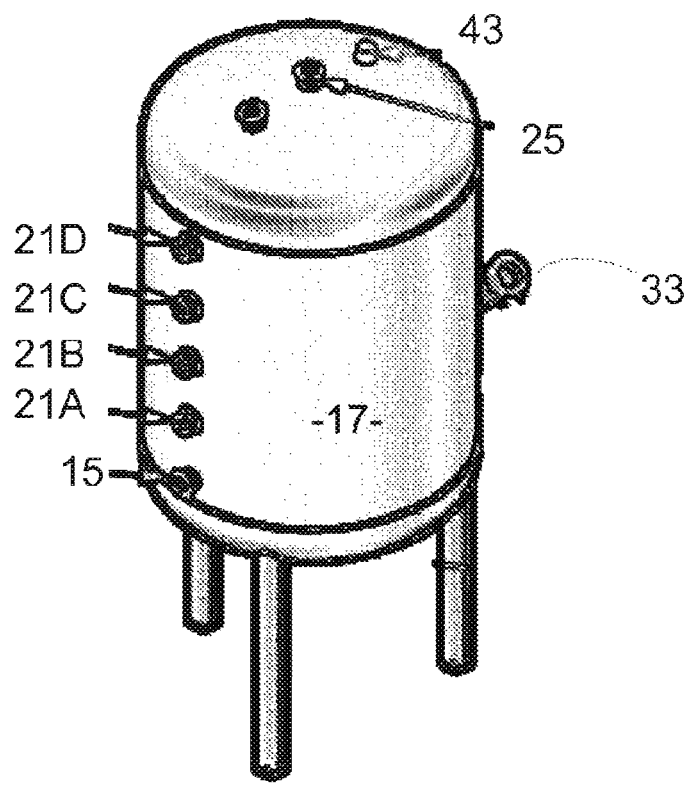
FIG. 2 is a perspective view of a treatment vessel according to the invention.

As can be seen in FIGS. 1 and 2, the heat treatment vessel 17 is equipped on its cylindrical wall 20 with four probes 21A, 21B, 21C and 21D for detecting the filling level.

As will be seen further on, for one treatment session, the heat treatment vessel will be filled to a level, located at the probe 21C.

Moreover, the facility comprises an air relief line 25, with a safety valve 26, the inlet of which is coupled to the crown 23 of the heat treatment vessel 17, therefore, level with the dome of the heat treatment vessel 17, and the outlet of which is coupled to the storage vessel 5.

Consequently, in the event of overpressure in the heat treatment vessel 17, the relieving action may take place directly into the storage vessel 5 so that there is no risk of contamination. Furthermore, expensive vents with filters that require regular maintenance inspections are thus avoided.

As can be seen in FIG. 1, the relief line 25 is coupled to the crown of the storage vessel 5 and continues via a tube 27 substantially parallel to the axis of the vessel 5 and projecting into this vessel 5 so that the outlet 29 of the relief line 25 immerses in the contaminated liquid in the filled state of this vessel 5. The length of the tube 27 is selected so that the outlet 29 is below the level of the liquid of this storage vessel 5.

Figure 3:
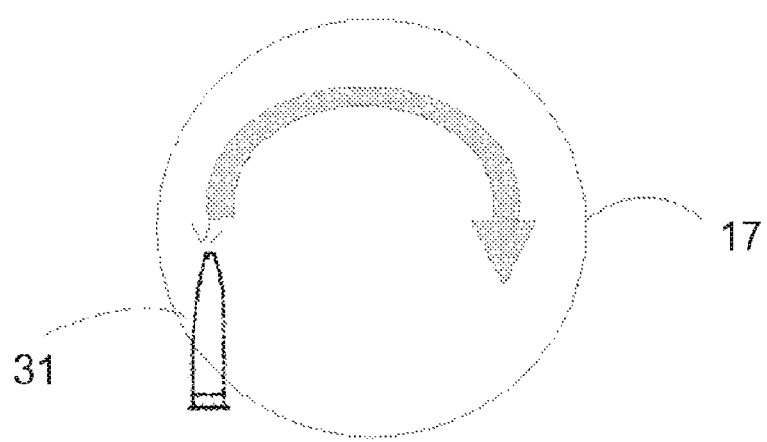
FIG. 3 is a schematic cross-sectional view of the vessel from FIG. 2, through the middle of the treatment vessel.

Furthermore, the heat treatment vessel 17 comprises at least one injector 31 of pressurized steam, for example of 5 bar (see FIGS. 1 and 3).

This injector 31 positioned so as to immerse in the liquid contaminated by pathogenic agents when the vessel is filled to the predetermined level, that is to say at the probe 21C (roughly ¾ of the total volume of the heat treatment vessel 17) and pointed toward the inside of the vessel 17 with at least one tangential component, or even completely tangentially relative to the cylindrical wall of the vessel 17 so as to create a cyclonic movement of the liquid to be decontaminated when pressurized steam is injected via the injector 31.

For this purpose, the injector 31 is borne by a support tube 33, one end of which is connected via a control valve 35 to a pressurized steam line. This support tube 33 passes through the wall 20 of the vessel 17 and juts out while being pointed toward the bottom 19 and bears, at its free end, the injector 31.

The expression "tangential component" should be understood to mean a component that is perpendicular to a radial direction relative to the axis of revolution of the heat treatment vessel 17.

Furthermore, according to the example of the figures, the injector 31 is pointed toward the inside of the vessel 17 with at least one component parallel to the axis of cylindrical revolution of the vessel 17, more specifically, the injector 31 is pointed upward, including in particular an angle $\alpha$ of between 60° and 80°, in particular of 70° with the cylindrical axis of the vessel.

According to one variant that is not shown, the injector 31 may be pointed downward in the direction of the bottom 19 of the vessel 17.

According to yet another variant, several injectors may be provided, either mounted on a single support tube, or each injector is mounted on an individual support tube.

In order to limit vibrations and the generation of noise during the injection of steam, a vibration damper 41 is positioned between the cylindrical wall 20 of the vessel 17 and the support tube 33.

A temperature probe 43 is also installed at the crown 23 of the vessel 17. This probe 43 is connected to the control valve 35 in order to control, for example, the injection of pressurized steam as a function of the temperature.

An outlet level with the bottom 19 of the heat treatment vessel 17 is coupled via a pipe 45 to an inlet of a heat exchanger 47 intended to cool the decontaminated liquid at the outlet of the heat treatment vessel 17.

The heat exchanger 47 has two inlets, a decontaminated fluid inlet 49, a cooling water inlet 51 and two outlets, a decontaminated and cooled liquid outlet 53 and an outlet 55 for water that has been used as cooling liquid in the heat exchanger 23. Thus, the cooling water system is always separated from the pipes of the decontaminated liquid so that there is no possibility of a return contamination, which further increases the safety of the facility 1 described here.

As is seen in FIG. 1 represented schematically, the heat exchanger 47 is of elongated shape in order to maximize the exchange surfaces and is positioned below the heat treatment vessel 17 so that the outgoing decontaminated liquid can pass by gravity without any intervention of a pump.

A control valve 57 (FIG. 1) positioned in the pipe 45 makes it possible to control the flow, for example for discharging the heat treatment vessel 17.

An example of the operation of the facility 1 described above will now be described.

Figure 5:
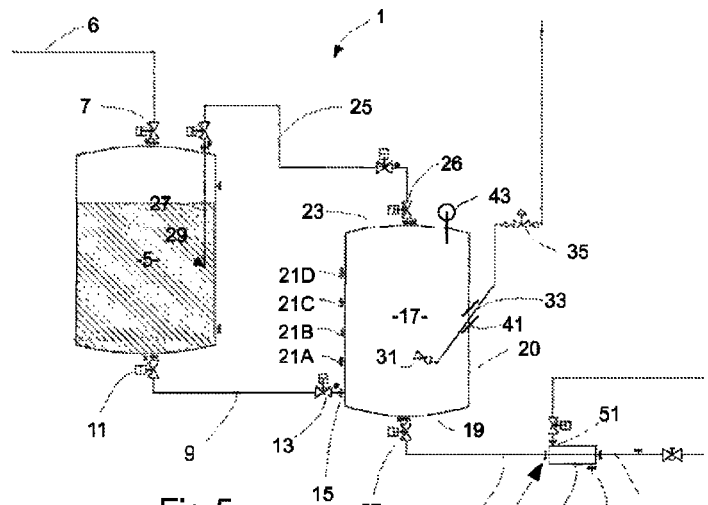
FIGS. 5 and 6 show the facility from FIG. 1 at various steps of the decontamination process.

This starts from the situation in FIG. 5, where the storage vessel is filled to around 80% with a liquid contaminated by pathogenic agents.

Figure 4:
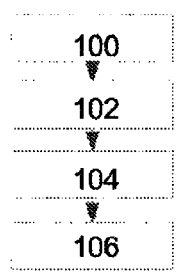
FIG. 4 is a flowchart showing an example of various steps of a decontamination process.
Figure 6:
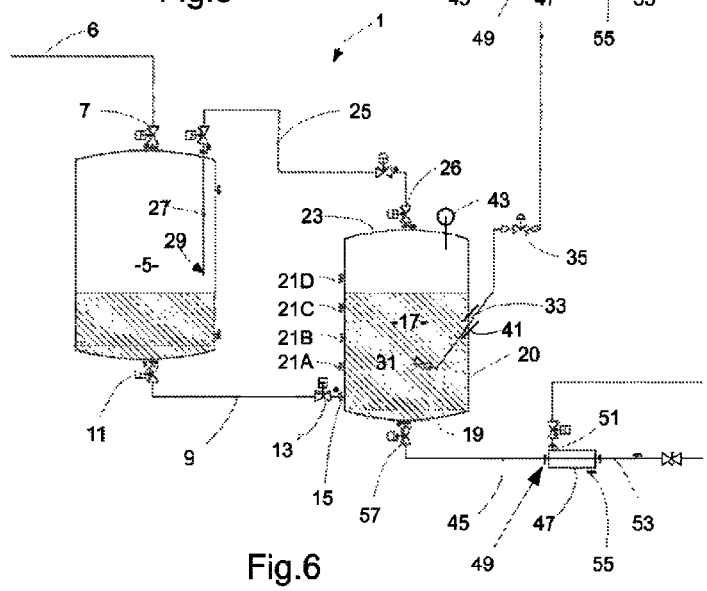

According to a first step 100 (see FIGS. 4 and 6), the heat treatment vessel 17 is filled with the contaminated liquid, via the principle of communicating vessels, up to the level located at the level probe 21C and therefore leaving a compression volume inside the treatment vessel 17 level with the dome. During this first step, the excess gaseous volume of the dome of the heat treatment vessel 17 is discharged via the relief line 25 into the storage vessel 5.

Next, according to a second step 102, steam at a pressure of 5 bar, for example, is injected into the contaminated liquid via the injector 31 in order to heat the contaminated liquid at a temperature between 130° C. and 140° C., preferably at 135° C. for a duration of between 4 min and 6 min, preferably for 5 min, allowing the pressure in the heat treatment vessel 17 to increase, for example here around 4 bar. The injection of steam by the injector 31 will create a cyclonic effect that makes it possible to homogenize the temperature of the liquid to be decontaminated. If the pressure in the heat treatment vessel 17 exceeds 4 bar, while the temperature is still below the setpoint temperature, the excess pressure is discharged via the relief line 25 into the storage vessel 5.

Lastly, according to a step 104, the liquid thus decontaminated is discharged with the aid of the pressure which is established during the heating and gravity.

Next, the decontaminated liquid is cooled, for example to around 60° C. during a step 106 in the heat exchanger 47.

It is therefore understood that the decontamination facility enables an effective decontamination and has an increased reliability. Furthermore, its maintenance is easy and does not present particular difficulties.

The invention claimed is:

1. A vessel for the heat treatment of pathogenic liquids in batches that is configured to be filled to a predetermined level while leaving a compression dome, the vessel comprising:
   at least one pressurized steam injector positioned below the predetermined level so as to be immersed in the liquid contaminated by pathogenic agents when the heat treatment vessel is filled to the predetermined level with the liquid contaminated by pathogenic agents,
   wherein the steam injector is pointed toward an inside of the heat treatment vessel with at least one tangential component so as to heat the liquid to be decontaminated and to create a cyclonic movement of the liquid contaminated by pathogenic agents to be decontaminated in order to homogenize the temperature of the liquid to be decontaminated without a movable mechanical element.

2. The vessel as claimed in claim 1, wherein said at least one injector is pointed perpendicular to a radial direction with respect to the axis of revolution of the heat treatment vessel.

3. The vessel as claimed in claim 1, wherein said at least one injector is pointed toward the inside of the heat treatment vessel with at least one component parallel to the axis of revolution of the vessel.

4. The vessel as claimed in claim 3, wherein the injector is pointed upward, with the axis of revolution of the vessel.

5. The vessel as claimed in claim 1, further comprising a support tube passing through the cylindrical wall of the heat treatment vessel and bearing said at least one injector.

6. The vessel as claimed in claim 5, further comprising a vibration damper positioned between the cylindrical wall of the heat treatment vessel and the tube.

7. The vessel as claimed in claim 5, further comprising filling level sensors positioned on the cylindrical wall of the heat treatment vessel.

8. A decontamination facility comprising:
   a vessel for storing the liquid contaminated by pathogenic agents,
   a heat treatment vessel as claimed in claim 1, the inlet of which is fluidically coupled to the outlet of the storage vessel, and
   a heat exchanger, the inlet of which is fluidically coupled to the outlet of the heat treatment vessel.

9. The decontamination facility as claimed in claim 8, wherein the storage vessel is positioned higher up relative to the heat treatment vessel, and in that the heat treatment vessel is positioned higher up relative to the heat exchanger so that the circulation of the pathogenic liquids in the facility is achieved by gravity.

10. The decontamination facility as claimed in claim 8, further comprising a relief line with a safety valve, the inlet of which is coupled level with the dome of the heat treatment vessel, and the outlet of which is coupled to the storage vessel.

11. The decontamination facility as claimed in claim 10, wherein the outlet of the relief line is located in the lower half of the storage vessel.

12. A process for decontaminating potentially pathogenic liquids in a heat treatment vessel as claimed in claim 1, wherein:
   the heat treatment vessel is filled with a liquid contaminated by pathogenic agents while leaving a gaseous expansion volume inside the treatment vessel,
   the liquid contaminated by pathogenic agents is heated at a temperature between 130° C. and 140° C. for a duration of between 4 min and 6 min by injecting pressurized steam, and
   the liquid thus decontaminated is discharged.

13. The process for decontaminating potentially pathogenic liquids as claimed in claim 12, wherein the pressure in the heat treatment vessel is allowed to increase to a pressure of around 4 bar.

* * * * *